United States Patent
Ikeda et al.

(10) Patent No.: US 7,295,652 B2
(45) Date of Patent: Nov. 13, 2007

(54) X-RAY IMAGE DIAGNOSTIC APPARATUS

(75) Inventors: Shigeyuki Ikeda, Kashiwa (JP); Shuji Sugeno, Moriya (JP); Tadashi Nakamura, Kashiwa (JP)

(73) Assignee: Hitachi Medical Corporation, Tokyo (JP)

(*) Notice: Subject to any disclaimer, the term of this patent is extended or adjusted under 35 U.S.C. 154(b) by 82 days.

(21) Appl. No.: 10/553,874

(22) PCT Filed: Apr. 23, 2004

(86) PCT No.: PCT/JP2004/005872

§ 371 (c)(1),
(2), (4) Date: Oct. 21, 2005

(87) PCT Pub. No.: WO2004/093685

PCT Pub. Date: Nov. 4, 2004

(65) Prior Publication Data
US 2006/0227935 A1    Oct. 12, 2006

(30) Foreign Application Priority Data
Apr. 23, 2003    (JP) .............................. 2003-117810

(51) Int. Cl.
*H05G 1/64* (2006.01)
(52) U.S. Cl. .............................. 378/98.12; 250/370.09; 382/274

(58) Field of Classification Search .................. 378/42, 378/62, 98.8–98.12, 114–116; 382/132, 382/274; 250/370.09
See application file for complete search history.

(56) References Cited

U.S. PATENT DOCUMENTS

| | | | | |
|---|---|---|---|---|
| 5,920,070 A | * | 7/1999 | Petrick et al. | 250/370.09 |
| 5,969,360 A | * | 10/1999 | Lee | 250/370.09 |
| 7,042,979 B2 | * | 5/2006 | Ikeda | 378/98.8 |
| 2003/0223539 A1 | * | 12/2003 | Granfors et al. | 378/98.8 |

FOREIGN PATENT DOCUMENTS

| JP | 2000-175892 | * | 6/2000 |
|---|---|---|---|
| JP | 2003-010159 | * | 1/2003 |

* cited by examiner

*Primary Examiner*—Jurie Yun
(74) *Attorney, Agent, or Firm*—Antonelli, Terry, Stout & Kraus, LLP.

(57) ABSTRACT

An X-ray image diagnostic apparatus including an X-ray source, an X-ray flat panel detector, an image processor, and an image display. The image processor includes a storage for storing plural sets of residual image data, acquired in advance from X-ray images in X-ray image acquisition modes from the X-ray flat panel detector before an actual measurement, in correspondence with the X-ray image acquisition modes, and a residual image corrector for correcting residual image data contained in an X-ray image in the actual measurement from the X-ray flat panel detector, using the residual image data stored in the storage.

10 Claims, 5 Drawing Sheets

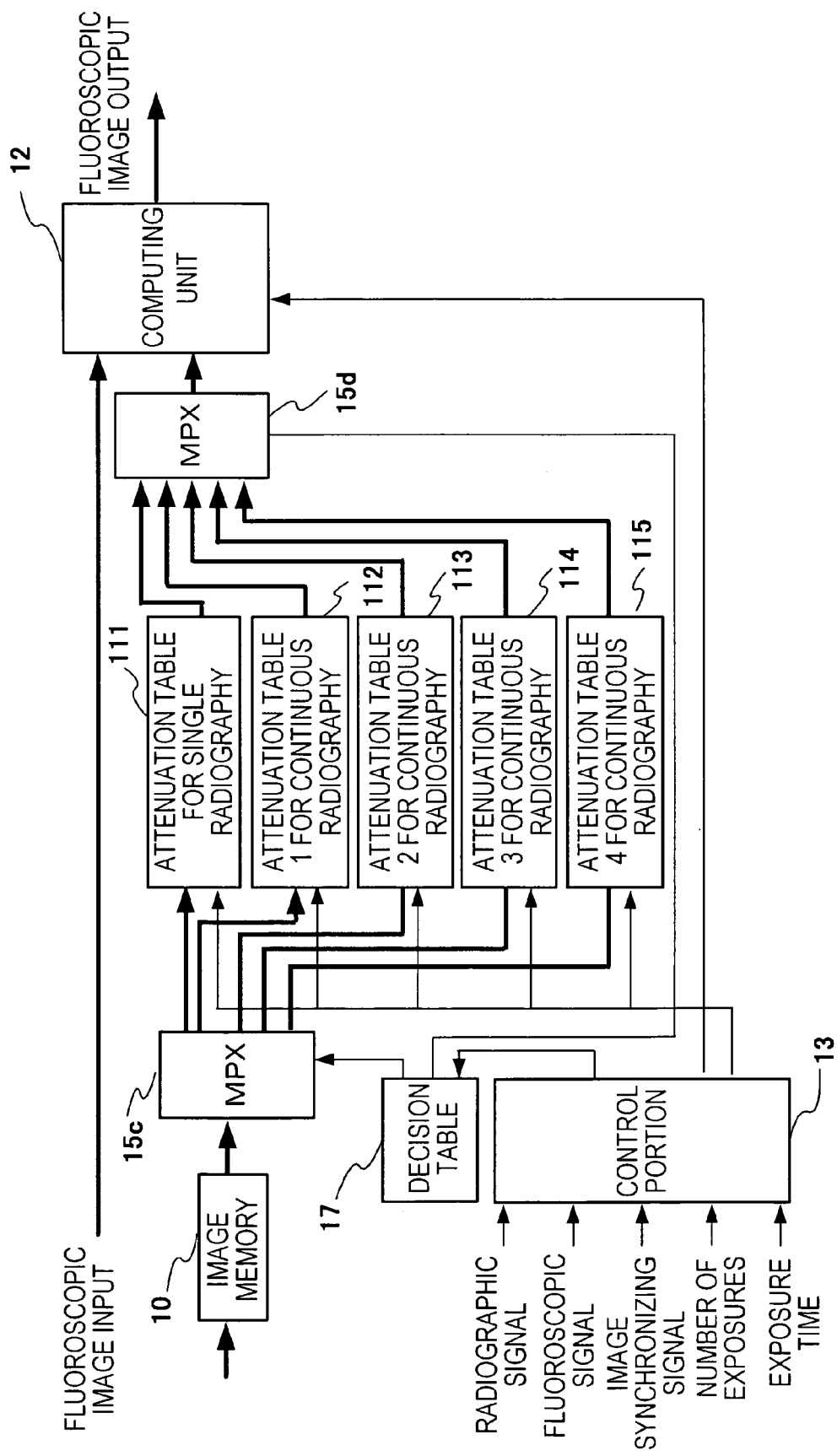

X-RAY IMAGE DIAGNOSTIC APPARATUS

TECHNICAL FIELD

The present invention relates to an X-ray image diagnostic apparatus that performs multiple radiography or fluoroscopy continuously, and to an X-ray image diagnostic apparatus in which a residual image of an X-ray image obtained by current radiography or fluoroscopy is corrected in real time.

BACKGROUND ART

An X-ray image diagnostic apparatus adopts an X-ray flat panel detector having an X-ray detector made of amorphous silicon, and residual image correction is necessary for the X-ray flat panel detector.

One example of residual image correction is described in JP-A-2001-243454 (public known reference). More specifically, a workstation takes samples on image data from a digital detector following the completion of first X-ray irradiation, so that attenuation of a residual image phenomenon is modeled. The workstation then predicts further attenuation of the residual image phenomenon on the basis of the modeled attenuation. The workstation thus corrects or compensates for attenuation of the residual image phenomenon in the following X-ray irradiation on the basis of the predicted attenuation.

The public known reference cited above, however, is silent about performing residual image correction in real time, because a prediction is made by acquiring residual image data, and processing time is necessary for acquisition and prediction.

DISCLOSURE OF THE INVENTION

An X-ray image diagnostic apparatus of the invention includes: an X-ray source that irradiates X-rays to a subject; an X-ray flat panel detector that is provided oppositely to the X-ray source and detects transmitted X-rays from the subject as an X-ray image; image processing means for applying image processing to the X-ray image detected by the X-ray flat panel detector; and image display means for displaying the X-ray image having undergone the image processing in the image processing means. The image processing means includes: storage means for storing plural sets of residual image data, acquired in advance from X-ray images in X-ray image acquisition modes from the X-ray flat panel detector before an actual measurement, in correspondence with the X-ray image acquisition modes; and residual image correction means for correcting residual image data contained in an X-ray image in the actual measurement from the X-ray flat panel detector, using the residual image data stored in the storage means.

It is thus possible to perform residual image correction of an X-ray image in real time.

According to one preferred embodiment of the invention, the image processing portion includes: an image memory that stores one frame of the residual image data from the X-ray flat panel detector; an attenuation quantity storage portion that stores quantities of attenuation of first and subsequent frames of the residual image data read out from the image memory; a computing unit that reads out the quantities of attenuation of the first and subsequent frames of the residual image data in response to a time on the basis of one frame of the residual image data stored in the image memory, and subtracts the read quantities of attenuation of the residual image data from a signal outputted from the X-ray flat panel detector; and a control portion that controls the image memory, the attenuation quantity storage portion, and the computing unit on the basis of respective signals, including control signals for each of the X-ray image acquisition modes including a radiographic signal and a fluoroscopic signal, and an image synchronizing signal to enable a display on the display means.

It is thus possible to address the attenuation characteristic of a residual image that varies in real time.

According to one preferred embodiment of the invention, the storage means stores plural frames of images of a residual image while X-rays are shielded after an X-ray image is acquired at a specific X-ray dose in advance.

It is thus possible to read out the residual image from the storage means according to the image synchronizing signal.

According to one preferred embodiment of the invention, the image processing means includes: plural image memories, each of which stores one frame of residual image data from the X-ray flat panel detector; plural attenuation quantity storage portions that store quantities of attenuation of first and subsequent frames of the residual image data read out from the image memories; a weight addition quantity storage portion that reads out quantities of attenuation of the first and subsequent frames of the residual image data in response to a time on the basis of one frame of the residual image data stored in each of the image memories, subjects the read quantities of attenuation of residual images to weighting addition depending on magnitude of a quantity of remaining residual images, and stores weight addition quantities; a computing unit that reads out the weight addition quantities stored in the weight addition quantity storage portion in response to a time, and subtracts the read weight addition quantities from a signal outputted from the X-ray flat panel detector; and a control portion that controls the image memories, the attenuation quantity storage portions, and the weight addition quantity storage portion on the basis of respective signals, including control signals for each of the X-ray image acquisition modes including a radiographic signal and a fluoroscopic signal, and an image synchronizing signal to enable a display on the display means.

It is thus possible to perform the residual image correction processing corresponding to the attenuation characteristic of a residual image that varies in real time even when a multiple-composite residual image is present.

According to one preferred embodiment of the invention, the image processing portion includes: an image memory that stores one frame of residual image data from the X-ray flat panel detector; a first switch that switches an output of a quantity of attenuation of an image of a residual image read out from the image memory depending on a read pixel matrix of the X-ray flat panel detector; plural attenuation quantity storage portions, each of which stores quantities of attenuation of first and subsequent frames of the residual image data on the basis of one frame from the image memory switched by the first switch, in correspondence with the read pixel matrix of the X-ray flat panel detector; a second switch that reads out a quantity of attenuation of a residual image stored in the attenuation quantity storage portions in response to a time, and makes a switch to the read quantity of attenuation of the residual image data; a computing unit that subtracts the quantity of attenuation of the residual image data switched by the second switch from a signal outputted from the X-ray flat panel detector; and a control portion that controls the image memory, the attenuation quantity storage portions, and the first and second switches on the basis of respective signals, including control signals for each of the X-ray image acquisition modes including a radiographic signal and a fluoroscopic signal, and an image synchronizing signal to enable a display on the display means.

It is thus possible to perform the residual image correction processing corresponding to the attenuation characteristic of a residual image that varies in real time even when the pixel unit read out from the X-ray flat panel detector is different.

According to one preferred embodiment of the invention, the image processing means includes: an image memory that stores one frame of residual image data from the X-ray flat panel detector; a first switch that switches an output of a quantity of attenuation of a residual image read out from the image memory depending on whether the X-ray image acquisition mode is a single radiographic mode or a continuous radiographic mode; plural attenuation quantity storage portions, each of which stores quantities of attenuation of first and subsequent frames of the residual image data on the basis of one frame from the image memory switched by the first switch, in correspondence with the single radiographic mode and the continuous radiographic mode; a second switch that reads out a quantity of attenuation of the residual image stored in the attenuation quantity storage portions in response to a time depending on the single radiographic mode or the continuous radiographic mode, and makes a switch to the read quantity of attenuation of the residual image; a computing unit that subtracts the quantity of attenuation of the residual image switched by the second switch from a signal outputted from the X-ray flat panel detector; and a control portion that controls the image memory, the attenuation quantity storage portions, and the first and second switches on the basis of respective signals, including control signals for each of the X-ray image acquisition modes including a radiographic signal and a fluoroscopic signal, and an image synchronizing signal to enable a display on the display means.

It is thus possible to perform the residual image correction processing corresponding to the attenuation characteristic of a residual image that varies in real time even the X-ray image acquisition mode is the radiographic mode that continues several times.

According to one preferred embodiment of the invention, the control portion determines a quantity of the residual image generated from continuous exposures in response to an exposure time in the continuous radiographic mode.

It is thus possible to perform the residual image correction processing corresponding to the attenuation characteristic of a residual image that varies in real time while taking a factor of a time of the radiographic mode that continues plural times into account.

BRIEF DESCRIPTION OF THE DRAWINGS

FIG. 6 is a block diagram showing an example of the configuration of the residual image correction processing portion capable of correcting residual images in both a non-continuous radiography (single) and a continuous radiography.

BEST MODE FOR CARRYING OUT THE INVENTION

Hereinafter, preferred embodiments of an X-ray image diagnostic apparatus of the invention will be described in detail with reference to the accompanying drawings.

Figure 1:
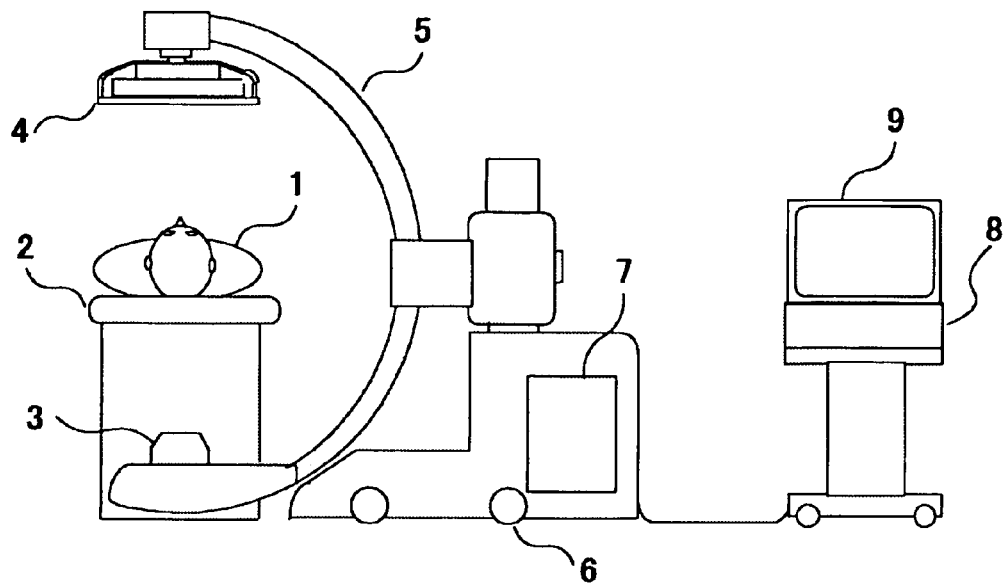
FIG. 1 is a block diagram common in respective embodiments of an X-ray image diagnostic apparatus of the invention.

As is shown in FIG. 1, an X-ray image diagnostic apparatus comprises an X-ray source 3, such as an X-ray tube, that generates X-rays, an X-ray flat panel detector 4 placed oppositely to the X-ray source 3, a C-arm 5 that supports the X-ray source 3 and the X-ray flat panel detector 3, a leg portion 6 that holds the C-arm 5 to stand on the floor, an X-ray generation high-voltage power source 7 that is electrically connected to the X-ray source 3, an image processing portion 8 that is electrically connected to the X-ray flat panel detector 3, and an image display portion (monitor) 9 that is electrically connected to the image processing portion 8.

The X-ray source 3 irradiates X-rays to a subject 1 lying on a diagnostic table 2. Conditions of the X-ray irradiation are conditionally selected by an operator using an unillustrated operation console or the like. The conditional-selection relates to X-ray irradiation conditions in X-ray image acquisition modes, for example, the fluoroscopic mode and the radiographic mode.

The X-ray flat panel detector 4 detects X-rays having passed through the subject 1 as an X-ray image. The conditions of the X-ray detection are conditionally selected by the operator of the apparatus using the unillustrated operation console or the like as with the case of the X-ray source 3. The conditional-selection relates to X-ray detection conditions in the X-ray image acquisition modes, and includes, for example, a (1×1) mode to read out detection elements that form the X-ray detector one by one, and a (2×2) mode to read out the detection elements alternately. The X-ray flat plane detector 4 is one example of the X-ray detector, and is formed by laminating scintillator and amorphous semiconductor. Also, the X-ray detector is not limited to the X-ray flat panel detector 4, and any detector of a type in which detection of X-rays gives rise to a residual image is included in a technique disclosed in this embodiment.

The C-arm 5 is supported on the leg portion 6, and is able to rotate and move in parallel while maintaining the X-ray source 3 and the X-ray flat panel detector 4 in the relation of being oppositely placed. The X-ray generation high-voltage power source 7 supplies the X-ray source 4 with power. The image processing portion 8 receives an X-ray image detected in the X-ray flat panel detector 4 as an input, and performs image processing, such as filtering, so that an X-ray image suitable for diagnosis is displayed on the monitor 9. The image processing portion 8 includes a memory to store an image to be processed. The monitor 9 displays an X-ray image having undergone image processing in the image processing portion 8.

Figure 2:
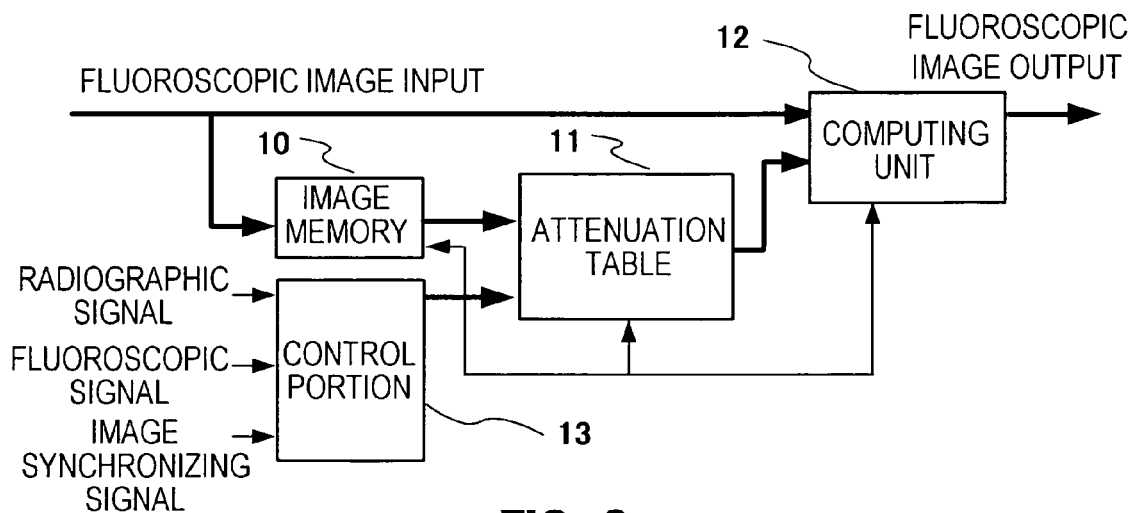
FIG. 2 is a block diagram showing a residual image correction processing portion incorporated in an image processing portion of FIG. 1.

A residual image correction processing portion shown as the first embodiment is incorporated in the image processing portion 8. As is shown in FIG. 2, the residual image correction processing portion includes an image memory 10 that is electrically connected to the X-ray flat panel detector 4, an attenuation table 11 that is electrically connected to the image memory 10, a computing unit 12 that is electrically connected to the X-ray flat panel detector 4 and the attenuation table 11, and a control portion 13 that is electrically connected to respective signals, including control signals for the respective modes, such as a radiographic signal and a fluoroscopic signal, and an image synchronizing signal that enables a display on the monitor 9, and is also electrically connected to the image memory 10, the attenuation table 11, and the computing unit 12.

Figure 3:
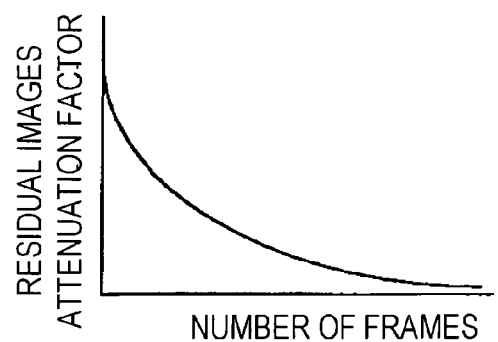
FIG. 3 is a view showing one example of residual image time attenuation factors stored in an attenuation table of FIG. 2 in graph form.

The image memory 10 stores an image in the fluoroscopic (radiographic) mode after X-ray irradiation ends in the radiographic (fluoroscopic) mode and before X-ray irradiation starts by switching to the fluoroscopic (radiographic) mode, that is, it stores one frame of a residual image. The image memory 10 acquires residual image data corresponding to an X-ray dose incident on the X-ray flat panel detector 3 during an exposure by storing an image after a pre-set time from the end of the exposure. The residual image data thus acquired is stored in the image memory 10 according to a radiographic signal (fluoroscopic signal) outputted from the X-ray generation high-voltage power source 7. The attenuation table 11 stores, as the attenuation characteristic, quantities of attenuation corresponding to the pixel positions of a fluoroscopic image immediately after an image of the residual image is stored in the image memory 10, that is, from first and subsequent frames. The attenuation characteristic can be visualized in graph form as shown in FIG. 3, using the ordinate for a quantity of attenuation and the abscissa for a time elapsed since the residual image was stored in the image memory 10 (number of frames). An exposure is performed at a specific X-ray dose in advance, and images of a residual image of plural frames are stored successively in the attenuation table 11 while X-rays are shielded, so that quantities of attenuation of these images of the residual image can be read out in response to a specific X-ray dose. The specific X-ray dose referred to herein is determined by various X-ray doses assumed in fluoroscopy or radiography. That is, by measuring residual image data while varying an X-ray dose in various manners, it is possible to create an attenuation table corresponding to the residual image data that differs with a varied X-ray dose. Plural frames of residual image data that keeps varying can be thereby acquired according to the image synchronizing signal. The computing unit 12 subtracts the residual image data that attenuates with time as is shown in the attenuation table from a fluoroscopic image after the exposure. A fluoroscopic image from which the residual image is removed or reduced can be thus found.

Operations of the X-ray image diagnostic apparatus of the first embodiment will now be described. Herein, a case where the X-ray image acquisition mode, in which an X-ray image is acquired, is switched from the radiographic mode to the fluoroscopic mode will be described. The attenuation table 11 has stored images (images of an attenuating residual image) in the last or before the last radiographic mode that attenuate with time. The images of the attenuating residual image keep attenuating with time since the mode is switched to the fluoroscopic mode. The X-ray source 3 irradiates X-rays to the subject 1 lying on the diagnostic table 2 under the X-ray irradiation conditions in the fluoroscopic mode. The X-ray flat panel detector 4 detects X-rays having passed through the subject 1 as a fluoroscopic image. The residual image correction processing portion stores a residual image after a pre-set time since the last or before the last X-ray image acquisition mode (for example, radiographic mode) ended, frame by frame in the image memory 10. The image of the residual image stores a radiographic signal or a fluoroscopic signal outputted from the X-ray generation high-voltage power supply 7. The computing unit 12 subtracts a quantity of attenuation of the residual image from the fluoroscopic image on which a quantity of the residual image corresponding to the frames after the radiographic mode is superimposed, and thereby finds a fluoroscopic image from which the residual image is reduced or removed. The monitor 9 displays the fluoroscopic image from which the residual image is reduced or removed.

As has been described, according to the X-ray image diagnostic apparatus of the first embodiment, it is possible to address the attenuation characteristic of a residual image that varies in real time. To be more concrete, the residual image correction processing portion includes the attenuation table 11 having stored attenuation information of plural residual images in the X-ray flat panel detector 4 that correspond to the respective fluoroscopic and radiographic modes, and the computing unit 12 that performs correction computation of a residual image that attenuates with time on the basis of the attenuation information of the residual images in the X-ray flat panel detector 4 stored in the attenuation table 11. The computing unit 12 therefore carries out correction computation of the residual image that attenuates with time on the basis of the attenuation information of the plural residual images in the X-ray flat panel detector 4 corresponding to the respective fluoroscopic and radiographic modes stored in the attenuation table 11. It is thus possible to perform residual image correction processing corresponding to the attenuation characteristic of a residual image that varies in real time.

Figure 4:
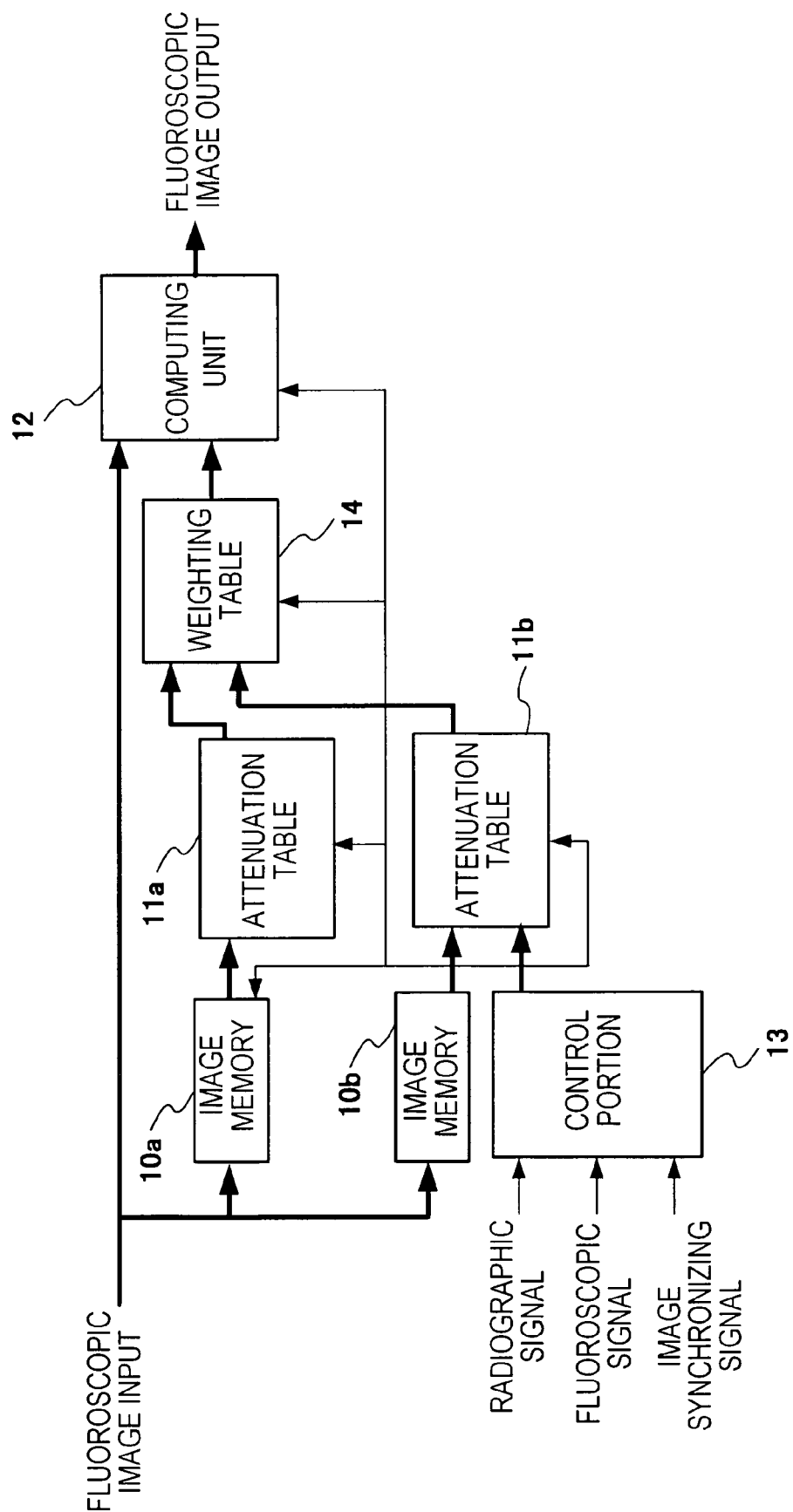
FIG. 4 is a block diagram showing an example of the configuration of the residual image correction processing portion when the following exposure is performed before a residual image disappears.

A case where a second radiographic mode is performed while a residual image of a first radiographic mode is present, and a fluoroscopic mode is further performed in a third exposure will now be described as a second embodiment with reference to FIG. 4. Herein, a residual image that resides due to the first radiographic mode is also referred to as a secondary residual image. Differences of the second embodiment from the first embodiment can be readily understood as follows by comparing FIG. 2 with FIG. 4. Differences are: two image memories 10a and 10b and two attenuation tables 11a and 11b are included instead of the image memory 10 and the attenuation table 11; a weighting table 14 that stores the two attenuation tables 11a and 11b after weighting processing is included; and the computing unit 12 finds residual image data that needs to be removed, from a result of the weighting addition processing using the weighting table 14. This is the case where two attenuation tables are prepared; however, the invention is not limited to this configuration. Three or more attenuation tables may be prepared, so that residual image data that needs to be removed is found from a result of weighting addition of respective results.

Operations of the X-ray image diagnostic apparatus of the second embodiment will now be described. In a first radiographic mode, the control portion 13 controls the weighting table 14 to output all the outputs from the attenuation table 11a to the computing unit 12. When a second radiographic mode is performed subsequently, an image of a residual image is recorded in the image memory 10b, and a quantity of the residual image is computed using the attenuation table 11b separately from a calculation of a quantity of the residual image using the image of the residual image recorded in the image memory 10a, and the result of computation is outputted to the weighting table 14. In the weighting table 14, a weight to a quantity of the residual image in the second exposure is increased for an image region where there are no or fewer residual image components of the first exposure. In a case where there are many residual image components in the first radiographic mode, and residual image components in the second radiographic mode are fewer, a weight of the residual image components in the first radiographic mode is increased. In short, a weight can be added in response to quantities of residual image components in the first radiographic mode and residual image components in the second radiographic mode.

As has been described, according to the X-ray image diagnostic apparatus of the second embodiment, even when a multiple-composite residual image is present, it is possible to provide an X-ray image diagnostic apparatus capable of performing residual image correction processing corresponding to the attenuation characteristic of a residual image that varies in real time. To be more concrete, even when a composite residual image, resulted from a case where the second radiographic mode is carried out before a residual image of the first radiographic mode disappears completely, gives influences to a fluoroscopic mode carried out in a third exposure, it is possible to achieve residual image correction processing corresponding to the attenuation characteristic of a residual image that varies in real time.

Also, about 120 to 150 sec. later, a quantity of the residual image often gives substantially no influences to the following X-ray image acquisition mode. Hence, in a case where the radiographic mode and the fluoroscopic mode are repeated frequently, by omitting weighting addition in the X-ray image acquisition mode that no longer gives influences, a quantity of the composite residual image can be found at high speeds by weighting addition.

Figure 5:
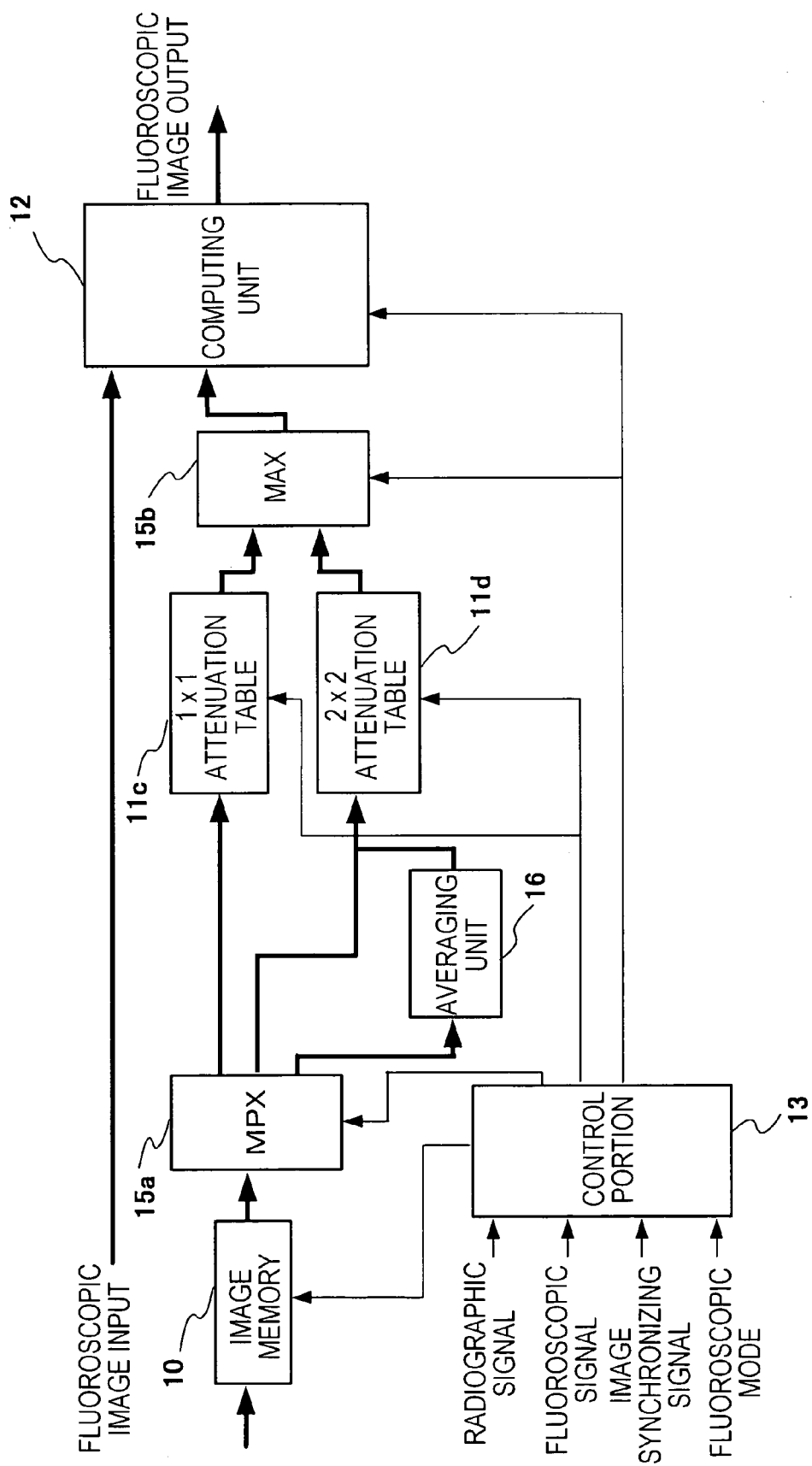
FIG. 5 is a block diagram showing an example of the configuration of the residual image correction processing portion in which (1×1) to read out pixels one by one and (2×2) to average four pixels and read them out as a whole as one pixel are attenuation tables.

A case where a pixel unit read out from the X-ray flat panel detector is different will now be described as a third embodiment with reference to FIG. 5. Herein, in a case where an image of the same portion of the subject is to be acquired, a high-definition fluoroscopic mode (1×1 read fluoroscopic mode) by which, although a display speed is slow due to a large volume of process data involved in image display, a fluoroscopic image can be obtained at high definition, and a fast fluoroscopic mode (2×2 read fluoroscopic mode) by which, although definition is deteriorated due to a small volume of process data involved in image display, a fluoroscopic image can be obtained at a high display speed, will be described by way of example. The 1×1 read fluoroscopic mode is a mode by which respective detection elements forming the X-ray flat panel detector are read out one by one. The 2×2 read fluoroscopic mode is a mode by which four pixels of each 2×2 matrix of respective detection elements forming the X-ray flat panel detector are added up, and a resultant added one pixel is read out. A data volume is therefore reduced to ¼ of that in the 1×1 read fluoroscopic mode. In addition, the high-definition fluoroscopic mode and the fast fluoroscopic mode in generalized versions of the foregoing are not limited to 1×1 and 2×2, and can be applied to various pixel sizes of 3×3, 4×4, etc.

Differences of the third embodiment from the first embodiment can be readily understood as follows by comparing FIG. 2 with FIG. 5. Differences are: attenuation tables 11c and 11d, respectively, for the 1×1 read fluoroscopic mode and the 2×2 read fluoroscopic mode are included instead of the attenuation table 11; multiplexers 15a and 15b that switch an image signal for each pixel read unit of the X-ray flat panel detector are included; an averaging unit 16 that averages four pixels of 1×1 for residual image data in the 1×1 read fluoroscopic mode to be used in the 2×2 read fluoroscopic mode, is included; the computing unit 12 finds a residual image that needs to be removed using read pixels switched by the multiplexer 15b; and the control portion 13 additionally receives, as an input, a fluoroscopic mode signal that determines 1×1 or 2×2 read pixels, and the control portion 13 operates according to the input signal.

Operations of the X-ray image diagnostic apparatus of the third embodiment will now be described. When the 2×2 read fluoroscopic mode is carried out after an exposure, the control portion 13 controls the multiplexer 15a in such a manner that an output from the image memory 10 is inputted to the attenuation table 11d for the 2×2 read fluoroscopic mode. Correction means same as in the first embodiment is thus applied to an image in the 2×2 read fluoroscopic mode. Likewise, when the 1×1 read fluoroscopic mode is carried out, the control portion 13 controls the multiplexer 15a in such a manner that an output from the image memory 10 is inputted to the attenuation table 11c for 1×1. Correction means same as in the first embodiment is thus applied to an image in the 1×1 read fluoroscopic mode. Incidentally, when the read pixel size is changed during fluoroscopy, conversion is necessary because an image recorded in the image memory 10 and a fluoroscopic image that needs correction are of different sizes. When the 2×2 read fluoroscopic mode is carried out before an exposure, residual image data in the 2×2 read fluoroscopic mode is recorded in the image memory 10. Likewise, when the 1×1 read fluoroscopic mode is carried out, residual image data in the 1×1 read fluoroscopic mode is recorded in the image memory 10. Normally, fast processing is required for a fluoroscopic image, and an input to the image processing portion 8 is handled in a size of the 2×2 read fluoroscopic mode. The image memory 10 therefore has a recording size of the 2×2 read fluoroscopic mode, too. In this case, when the fast fluoroscopic mode is switched to the high-definition fluoroscopic mode, the 2×2 read fluoroscopic mode is carried out before an exposure, and the 2×2 read fluoroscopic mode is changed to the 1×1 fluoroscopic mode after the exposure. Of the residual image data recorded in the image memory 10, data of an image region in the 1×1 read fluoroscopic mode is sent to the attention table 11c for the 1×1 read fluoroscopic mode. This is because when data of the image region alone is sent, high definition is maintained and yet a rate of processing speed can be taken into account by optimizing a data volume. In this instance, a single pixel in the residual image data in the 2×2 read fluoroscopic mode stored in the image memory 10 is inputted to four pixels at positions corresponding to this pixel in the residual image data in the 1×1 read fluoroscopic mode within the attenuation table 11c. Also, the 1×1 read fluoroscopic mode is carried out before an exposure, and 1×1 exposure is carried out subsequently. Further, when the 1×1 read fluoroscopic mode is changed to the 2×2 read fluoroscopic mode after this exposure, neighboring four pixels within the image memory 10 are averaged before being input to the attenuation table, and then outputted to the 2×2 attenuation table 11d.

As has been described, according to the X-ray image diagnostic apparatus of the third embodiment, even when a pixel unit read out from the X-ray flat panel detector is different, it is possible to perform residual image correction processing corresponding to the attenuation characteristic of a residual image that varies in real time.

A case where the radiographic mode is continued will now be described as a fourth embodiment with reference to FIG. 6. Herein, cases where the radiographic mode, in which a considerable residual image resides, is carried out a single time and repeated plural times will be described separately.

Differences of the fourth embodiment from the first embodiment can be readily understood as follows by comparing FIG. 2 with FIG. 6. Differences are: an attenuation table 111 for a single radiographic mode and attenuation tables 1 through 4 (112 to 115) for a continuous radiographic mode are included instead of the attenuation table 11; multiplexers 15c and 15d that switch an image signal to the table for the single radiographic mode or to the tables 1 through 4 for the continuous radiographic mode are included; the computing unit 12 removes a residual image in the single radiographic mode or the continuous radiographic mode switched by the multiplexer 15d; the control portion 13 receives, as inputs, the number of continuous exposures together with an exposure time of each, and operates according to the input signal; and a decision table that generates a selection signal of the multiplexers 15c and 15d using an output signal from the control portion 13, is included.

Operations of the X-ray image diagnostic apparatus of the fourth embodiment will now be described. An image of the residual image in a first radiographic mode is recorded in the image memory 10, the residual image data is found using the attenuation table 111, and a fluoroscopic image from which the residual image is removed is outputted by subtracting the resultant residual image data from the fluoroscopic image, all of which are the same as in the first embodiment. In this embodiment, attenuation coefficients for a single radiography same as those in the first embodiment are stored in the attenuation table 111. As are shown in FIG. 6, different tables, each having different attenuation factors for a continuous radiography, are inputted into the attenuation tables 112, 113, 114, and 115. For the continuous radiography, an image memory value, an incident dose, an elapsed time since the exposure, the number of exposures, and intervals of exposures are necessary as parameters to specify the attenuation factor. Of these, an image memory value, an incident dose, and an elapsed time since the exposure are also used in the attenuation table for the single radiographic mode. Hence, the number of exposures and intervals of exposures are also necessary as parameters for the attenuation tables for the continuous radiographic mode. However, it is difficult to include a table having all these parameters in terms of packaging of the circuit, and exact correction using the number of exposures and intervals of exposures is enabled by preparing plural attenuation tables for the continuous radiographic mode.

As has been described, according to the X-ray image diagnostic apparatus of the fourth embodiment, even when the X-ray image acquisition mode is the radiographic mode that continues plural times, it is possible to perform residual image correction processing corresponding to the attenuation characteristic of a residual image that varies in real time.

Figure 7A:
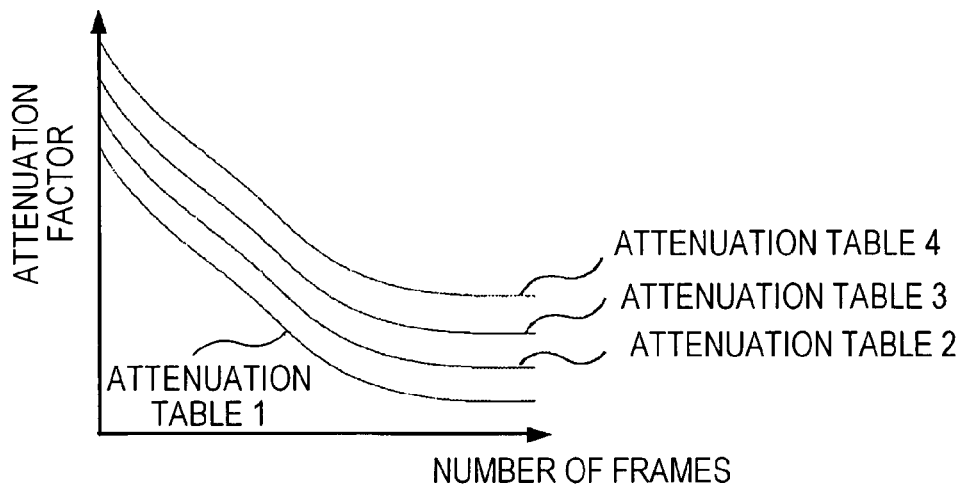
FIGS. 7A, 7B and 7C are used to describe an example of settings of selection conditions of residual images stored in attenuation tables 1 through 4 for the continuous radiography of FIG. 6.

A case where four attenuation tables 112 through 115 for the continuous radiography as are shown in FIG. 7A will now be described. An evaluation function, to which a weight is added at every certain time before the fluoroscopy begins, is used as a selection method of respective tables. This method will now be described.

Let a function f(x) expressed as Equation (1) be an evaluation function:

$$f(x)=5f0+2f1+1f2 \qquad (1)$$

where f0, f1, and f2 are the number of exposures in times t0, t1, and t2 obtained by dividing a time immediately before the exposure ends.

Figure 7B:
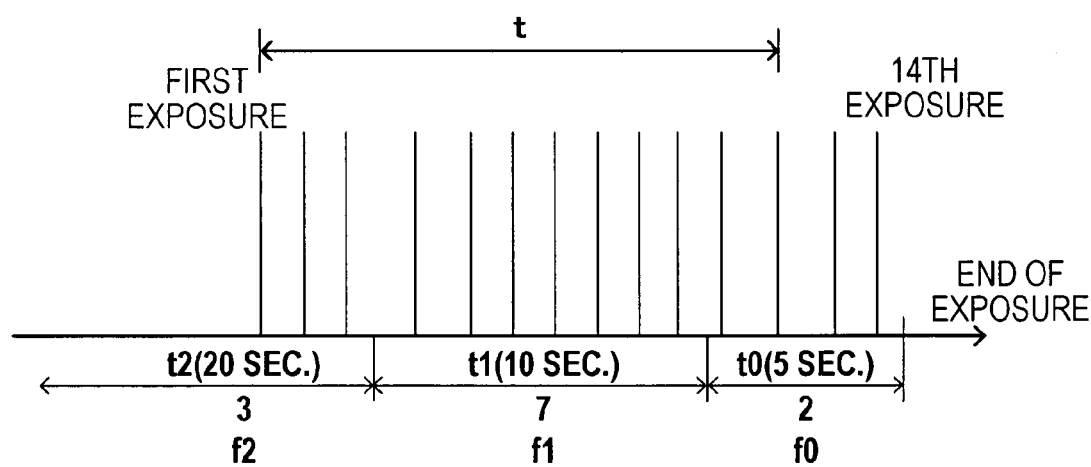

In a case where 14 exposures are performed continuously for 25 sec. as is shown in FIG. 7B, the time is divided to 20 sec., 10 sec., and 5 sec., and how many times exposures are performed within each divided time is stored. When two in f0, seven in f1, and three in f2, then f(x)=5×2+2×7+1×3=27 sec.

Figure 7C:
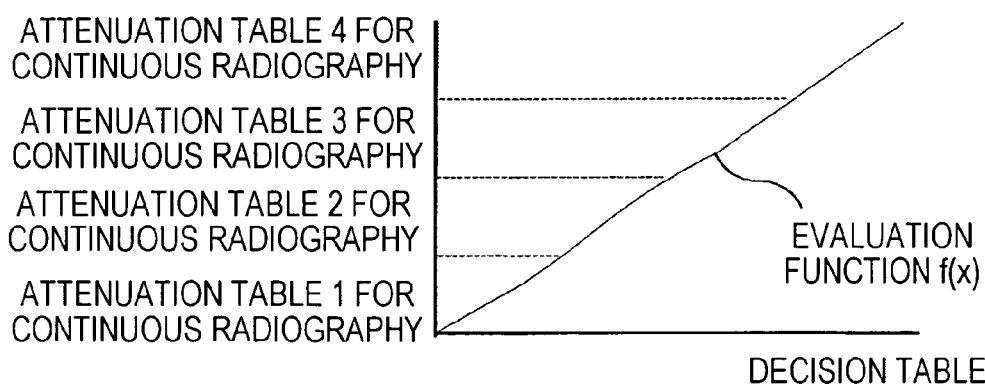

This value is inputted into a decision table 17 shown in FIG. 7C, and a continuous table corresponding to f(x) is selected. For example, when $0 \leq f(x) \leq 10$, the continuous table 1 is selected, and when $11 \leq f(x) \leq 20$, the continuous table 2 is selected. The residual image data selected during the continuous radiography is thus determined.

It is thus possible to perform residual image correction processing corresponding to the attenuation characteristic of a residual image that varies in real time while taking into account a factor of the time for the radiographic mode that continues plural times.

Also, by increasing the attenuation tables for the continuous radiography as needed, exact correction is enabled for each interval of exposures and each number of exposures.

In plural embodiments described above, for an examination of a digestive tube or the like, the need to acquire a current fluoroscopic image immediately after the acquisition of an image of the last exposure can be satisfied.

Further, in the plural embodiments described above, it is possible to address a composite residual image resulted from multiple radiography or and fluoroscopy.

INDUSTRIAL APPLICABILITY

The invention provides an X-ray image diagnostic apparatus capable of performing residual image processing corresponding to the attenuation characteristic of a residual image that varies in real time.

The invention claimed is:

1. An X-ray image diagnostic apparatus, characterized by comprising:
   an X-ray source that irradiates X-rays to a subject;
   an X-ray flat panel detector that is provided oppositely to the X-ray source and detects transmitted X-rays from the subject as an X-ray image;
   image processing means for applying image processing to the X-ray image detected by the X-ray flat panel detector; and
   image display means for displaying the X-ray image having undergone the image processing in the image processing means,
   wherein the image processing means includes:
      storage means for storing plural sets of residual image data that attenuate with time, acquired in advance from X-ray images in X-ray image acquisition modes from the X-ray flat panel detector before an actual measurement, in correspondence with the X-ray image acquisition modes;
      an image memory that stores one frame of the residual image data, which is obtained in a fluoroscopic mode after X-ray irradiation ends in a radiograph mode and before X-ray irradiation starts by switching to the fluoroscopic mode, from the X-ray flat panel detector;
      a computing unit that reads out quantities of attenuation of the first and subsequent frames of the residual image data in response to time on a basis of one frame of the residual image data stored in the image memory, and subtracts the read quantities of attenuation of the residual image data from a signal outputted from the X-ray flat panel detector; and
      a control portion that controls the image memory, an attenuation quantity storage portion, and the computing unit on a basis of respective signals, including control signals for each of the X-ray image acquisition modes including a radiographic signal and a fluoroscopic signal, and an image synchronizing signal to enable a display on the display means.

2. The X-ray image diagnostic apparatus according to claim 1, wherein:
   the storage means stores plural frames of images of a residual image while X-rays are shielded after an X-ray image is acquired at a specific X-ray dose in advance.

3. The X-ray image diagnostic apparatus according to claim 1, wherein the image processing means includes:
   plural image memories, each of which stores one frame of residual image data from the X-ray flat panel detector;
   plural attenuation quantity storage portions that store quantities of attenuation of first and subsequent frames of the residual image data read out from the image memories;
   a weight addition quantity storage portion that reads out quantities of attenuation of the first and subsequent frames of the residual image data in response to a time on the basis of one frame of the residual image data stored in each of the image memories, subjects the read quantities of attenuation of residual images to weighting addition depending on magnitude of a quantity of remaining residual images, and stores weight addition quantities;
   a computing unit that reads out the weight addition quantities stored in the weight addition quantity storage portion in response to a time, and subtracts the read weight addition quantities from a signal outputted from the X-ray flat panel detector; and
   a control portion that controls the image memories, the attenuation quantity storage portions, and the weight addition quantity storage portion on the basis of respective signals, including control signals for each of the X-ray image acquisition modes including a radiographic signal and a fluoroscopic signal, and an image synchronizing signal to enable a display on the display means.

4. The X-ray image diagnostic apparatus according to claim 1, wherein the image processing portion includes:
   an image memory that stores one frame of residual image data from the X-ray flat panel detector;
   a first switch that switches an output of a quantity attenuation of an image of a residual image read out from the image memory depending on a read pixel matrix of the X-ray flat panel detector;
   plural attenuation quantity storage portions, each of which stores quantities of attenuation of first and subsequent frames of the residual image data on the basis of one frame from the image memory switched by the first switch, in correspondence with the read pixel matrix of the X-ray flat panel detector;
   a second switch that reads out a quantity of attenuation of a residual image stored in the attenuation quantity storage portions in response to a time, and makes a switch to the read quantity of attenuation of the residual image data;
   a computing unit that subtracts the quantity of attenuation of the residual image data switched by the second switch from a signal outputted from the X-ray flat panel detector; and
   a control portion that controls the image memory, the attenuation quantity storage portions, and the first and second switches on the basis of respective signals, including control signals for each of the X-ray image acquisition modes including a radiographic signal and a fluoroscopic signal, and an image synchronizing signal to enable a display on the display means.

5. The X-ray image diagnostic apparatus according to claim 1, wherein the image processing means includes:
an image memory that stores one frame of residual image data from the X-ray flat panel detector;
a first switch that switches an output of a quantity of attenuation of a residual image read out from the image memory depending on whether the X-ray image acquisition mode is a single radiographic mode or a continuous radiographic mode;
plural attenuation quantity storage portions, each of which stores quantities of attenuation of first and subsequent frames of the residual image data on the basis of one frame from the image memory switched by the first switch, in correspondence with the single radiographic mode and the continuous radiographic mode;
a second switch that reads out a quantity of attenuation of the residual image stored in the attenuation quantity storage portions in response to a time depending on the single radiographic mode or the continuous radiographic mode, and makes a switch to the read quantity of attenuation of the residual image;
a computing unit that subtracts the quantity of attenuation of the residual image switched by the second switch from a signal outputted from the X-ray flat panel detector; and
a control portion that controls the image memory, the attenuation quantity storage portions, and the first and second switches on the basis of respective signals, including control signals for each of the X-ray image acquisition modes including a radiographic signal and a fluoroscopic signal, and an image synchronizing signal to enable a display on the display means.

6. The X-ray image diagnostic apparatus according to claim 5, wherein:
the control portion determines a quantity of the residual image generated from continuous exposures in response to an exposure time in the continuous radiographic mode.

7. An X-ray image diagnostic apparatus, characterized by comprising:
an X-ray source that irradiates X-rays to a subject;
an X-ray flat panel detector that is provided oppositely to the X-ray source and detects transmitted X-rays from the subject as an X-ray image;
image processing means for applying image processing to the X-ray image detected by the X-ray flat panel detector; and
image display means for displaying the X-ray image having undergone the image processing in the image processing means,
wherein the image processing means includes:
storage means for storing plural sets of residual image data, acquired in advance from X-ray images in X-ray image acquisition modes from the X-ray flat panel detector before an actual measurement, in correspondence with the X-ray image acquisition modes; and
residual image correction means for correcting residual image data contained in an X-ray image in the actual measurement from the X-ray flat panel detector, using the residual image data stored in the storage means; and
plural image memories, each of which stores one frame of residual image data from the X-ray flat panel detector;
plural attenuation quantity storage portions that store quantities of attenuation of first and subsequent frames of the residual image data read out from the image memories;
a weight addition quantity storage portion that reads out quantities of attenuation of the first and subsequent frames of the residual image data in response to a time on the basis of one frame of the residual image data stored in each of the image memories, subjects the read quantities of attenuation of residual images to weighting addition depending on magnitude of a quantity of remaining residual images, and stores weight addition quantities;
a computing unit that reads out the weight addition quantities stored in the weight addition quantity storage portion in response to a time, and subtracts the read weight addition quantities from a signal outputted from the X-ray flat panel detector; and
a control portion that controls the image memories, the attenuation quantity storage portions, and the weight addition quantity storage portion on the basis of respective signals, including control signals for each of the X-ray image acquisition modes including a radiographic signal and a fluoroscopic signal, and an image synchronizing signal to enable a display on the display means.

8. An X-ray image diagnostic apparatus, characterized by comprising:
an X-ray source that irradiates X-rays to a subject;
an X-ray flat panel detector that is provided oppositely to the X-ray source and detects transmitted X-rays from the subject as an X-ray image;
image processing means for applying image processing to the X-ray image detected by the X-ray flat panel detector; and
image display means for displaying the X-ray image having undergone the image processing in the image processing means,
wherein the image processing means includes:
storage means for storing plural sets of residual image data, acquired in advance from X-ray images in X-ray image acquisition modes from the X-ray flat panel detector before an actual measurement, in correspondence with the X-ray image acquisition modes; and
residual image correction means for correcting residual image data contained in an X-ray image in the actual measurement from the X-ray flat panel detector, using the residual image data stored in the storage means; and
an image memory that stores one frame of residual image data from the X-ray flat panel detector;
a first switch that switches an output of a quantity attenuation of an image of a residual image read out from the image memory depending on a read pixel matrix of the X-ray flat panel detector;
plural attenuation quantity storage portions, each of which stores quantities of attenuation of first and subsequent frames of the residual image data on the basis of one frame from the image memory switched by the first switch, in correspondence with the read pixel matrix of the X-ray flat panel detector;
a second switch that reads out a quantity of attenuation of a residual image stored in the attenuation quantity storage portions in response to a time, and makes a switch to the read quantity of attenuation of the residual image data;
a computing unit that subtracts the quantity of attenuation of the residual image data switched by the second switch from a signal outputted from the X-ray flat panel detector; and
a control portion that controls the image memory, the attenuation quantity storage portions, and the first and second switches on the basis of respective signals, including control signals for each of the X-ray image acquisition modes including a radiographic signal and a fluoroscopic signal, and an image synchronizing signal to enable a display on the display means.

9. An X-ray image diagnostic apparatus, characterized by comprising:

an X-ray source that irradiates X-rays to a subject;

an X-ray flat panel detector that is provided oppositely to the X-ray source and detects transmitted X-rays from the subject as an X-ray image;

image processing means for applying image processing to the X-ray image detected by the X-ray flat panel detector; and image display means for displaying the X-ray image having undergone the image processing in the image processing means, wherein the image processing means includes:

storage means for storing plural sets of residual image data, acquired in advance from X-ray images in X-ray image acquisition modes from the X-ray flat panel detector before an actual measurement, in correspondence with the X-ray image acquisition modes; and residual image correction means for correcting residual image data contained in an X-ray image in the actual measurement from the X-ray flat panel detector, using the residual image data stored in the storage means; and an image memory that stores one frame of residual image data from the X-ray flat panel detector;

a first switch that switches an output of a quantity of attenuation of a residual image read out from the image memory depending on whether the X-ray image acquisition mode is a single radiographic mode or a continuous radiographic mode;

plural attenuation quantity storage portions, each of which stores quantities of attenuation of first and subsequent frames of the residual image data on the basis of one frame from the image memory switched by the first switch, in correspondence with the single radiographic mode and the continuous radiographic mode;

a second switch that reads out a quantity of attenuation of the residual image stored in the attenuation quantity storage portions in response to a time depending on the single radiographic mode or the continuous radiographic mode, and makes a switch to the read quantity of attenuation of the residual image;

a computing unit that subtracts the quantity of attenuation of the residual image switched by the second switch from a signal outputted from the X-ray flat panel detector; and a control portion that controls the image memory, the attenuation quantity storage portions, and the first and second switches on the basis of respective signals, including control signals for each of the X-ray image acquisition modes including a radiographic signal and a fluoroscopic signal, and an image synchronizing signal to enable a display on the display means.

10. The X-ray image diagnostic apparatus according to claim 9, wherein:

the control portion determines a quantity of the residual image generated from continuous exposures in response to an exposure time in the continuous radiographic mode.

* * * * *